(12) United States Patent
Katscher et al.

(10) Patent No.: US 12,174,282 B2
(45) Date of Patent: Dec. 24, 2024

(54) AUTOMATED DETECTION OF CRITICAL STATIONS IN MULTI-STATION MAGNETIC RESONANCE IMAGING

(71) Applicant: KONINKLIJKE PHILIPS N.V., Eindhoven (NL)

(72) Inventors: Ulrich Wolfgang Katscher, Norderstedt (DE); Peter Koken, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/925,034

(22) PCT Filed: Mar. 9, 2022

(86) PCT No.: PCT/EP2022/055962
§ 371 (c)(1),
(2) Date: Nov. 14, 2022

(87) PCT Pub. No.: WO2022/194624
PCT Pub. Date: Sep. 22, 2022

(65) Prior Publication Data
US 2023/0417853 A1    Dec. 28, 2023

(30) Foreign Application Priority Data
Mar. 15, 2021  (EP) .................................. 21162561

(51) Int. Cl.
*G01R 33/567* (2006.01)
*A61B 5/00* (2006.01)
(Continued)

(52) U.S. Cl.
CPC .......... *G01R 33/5673* (2013.01); *A61B 5/704* (2013.01); *G01R 33/283* (2013.01); *G01R 33/288* (2013.01); *G01R 33/58* (2013.01)

(58) Field of Classification Search
None
See application file for complete search history.

(56) References Cited

U.S. PATENT DOCUMENTS 10,512,417 B2 * 12/2019 Hannemann ......... G01R 33/283
2007/0225588 A1 * 9/2007 Steckner ................ G16H 30/20
600/407

(Continued)

FOREIGN PATENT DOCUMENTS

| EP | 3719520 A2 | 10/2020 |
|----|------------|---------|
| JP | 2007167283 A | 7/2007 |
| JP | 4822834 B2 | 11/2011 |

OTHER PUBLICATIONS

International Search Report and Written Opinion from PCT/EP2022/055962 mailed Jun. 1, 2022.
(Continued)

*Primary Examiner* — Rodney E Fuller

(57) ABSTRACT

A device is provided for detecting critical stations in a multi-station scan. The device includes an input unit, a processing unit, and an output unit. The input unit is configured to receive image data taken from a patient lying on a table before start of a diagnostic scan with a magnetic resonance imaging system. The processing unit is configured to analyze the image data of the patient to identify a spatial location of the lungs of the patient to align the spatial location of the lungs of the patient with a planned multi-station scan to identify the critical stations that are potentially affected by a respiratory motion of the patient, and to assign breath-hold to the identified critical stations. The output unit is configured to provide the identified critical stations. Thus, the selection of critical stations can be automatically and consistently satisfied without operator intervention.

20 Claims, 2 Drawing Sheets

(51) Int. Cl.
*G01R 33/28* (2006.01)
*G01R 33/58* (2006.01)

(56) References Cited

U.S. PATENT DOCUMENTS

| | | |
|---|---|---|
| 2009/0012385 A1 | 1/2009 | Takizawa et al. |
| 2014/0084921 A1 | 3/2014 | Horger et al. |
| 2016/0092078 A1* | 3/2016 | Braun .................... A61B 34/00 348/46 |
| 2016/0266760 A1* | 9/2016 | Beckmann ........... A61B 5/0033 |
| 2017/0082716 A1* | 3/2017 | Greiser .............. G01R 33/5673 |
| 2019/0057515 A1* | 2/2019 | Teixeira ................. A61B 6/488 |
| 2020/0015702 A1* | 1/2020 | Dumoulin ............ A61B 6/0487 |
| 2020/0258243 A1* | 8/2020 | Chang ................... A61B 5/704 |
| 2020/0309880 A1* | 10/2020 | Bi ........................ G01R 33/543 |

OTHER PUBLICATIONS

Zangos et al "First Experiences With Whole Body Dot Engine" Retrieved from the Internet Jan. 1, 2015, XP055747544 Clinical Abdominal Imaging.

Reiner et al "Whole Body Dot Engine: First Clinical Experience with Automated Chest, Abdomen and Pelvis Examiations" MAGNETOM Flash, Jan. 1, 2016, p. 31-33.

\* cited by examiner

AUTOMATED DETECTION OF CRITICAL STATIONS IN MULTI-STATION MAGNETIC RESONANCE IMAGING

CROSS REFERENCE TO RELATED APPLICATIONS

This application is a U.S. national phase application of International Application No. PCT/EP2022/055962 filed on Mar. 9, 2022, which claims the benefit of EP application Ser. No. 21162561.1 filed on Mar. 15, 2021 and is incorporated herein by reference.

FIELD OF THE INVENTION

The present invention relates to multi-station scan, and in particular to a device for detecting critical stations in a multi-station scan, to a magnetic resonance imaging system, to a method for detecting critical stations in a multi-station scan, to a computer program element, and to a computer readable medium.

BACKGROUND OF THE INVENTION

For whole-body imaging, a common approach is the multi-station scan, where different parts of the body in the longitudinal direction are measured sequentially and concatenated after the scan. The stations that might be affected by respiratory motion are marked for breath-hold.

Selection of stations potentially affected by respiratory motion is currently done manually by the technician based on visual inspection. This is a tedious and time-consuming procedure, contributing to limited patient throughput of the hospital.

SUMMARY OF THE INVENTION

There may be a need to improve selection of stations.

The object of the present invention is solved by the subject-matter of the independent claims, wherein further embodiments are incorporated in the dependent claims. It should be noted that the following described aspects of the invention apply also to the device for detecting critical stations in a multi-station scan, to the MRI system, to the method for detecting critical stations in a multi-station scan, to the computer program element, and to the computer readable medium.

According to a first aspect of the present invention, there is provided a device for detecting critical stations in a multi-station scan. The device comprises an input unit, a processing unit, and an output unit. The input unit is configured to receive image data taken from a patient lying on a table before start of a diagnostic scan with a magnetic resonance imaging system. The processing unit is configured to analyze the received image data of the patient to identify a spatial location of a lung of the patient, to align the spatial location of the lung of the patient with a planned multi-station scan to identify the critical stations that are potentially affected by a respiratory motion of the patient, and to assign breath-hold to the identified critical stations. The image data comprises an optical image captured by an optical camera. The output unit is configured to provide the identified critical stations.

In other words, it is proposed to analyze automatically an optical image, e.g. taken from the patient directly before moving the table into the bore or taken from the patient in the bore, such that areas are detected which bear a risk to be affected by respiratory motion (typically, in and around lung). These areas are compared with the different stations of the scan, and potentially affected stations are identified and assigned to breath-holding.

The optical camera may use visible and/or near infrared light to image the patient. In some examples, the optical camera may be a standard camera for capturing a two-dimensional optical image of the patient. In some other examples, the optical camera may be a ranging camera for capturing a depth image of the patient.

Thus, the selection of critical stations can be automatically and consistently satisfied without operator intervention. The tedious and time-consuming step of manually identifying and selecting stations potentially affected by respiratory motion can be avoided. This will be explained hereafter and in particular with respect to the example shown in FIG. 2.

According to an embodiment of the present invention, the image data comprises an optical image captured by an in-bore optical camera.

An example of the in-bore optical sensor is Philips Vitaleye. The in-bore optical camera may be arranged inside the top left plastic casing and focuses on the subject's upper body.

According to an embodiment of the present invention, the processing unit is configured to identify the spatial location of the lung of the patient by locating a thorax from the optical image based on landmark detection.

Spatial location of the lung may be identified using a body surface approximation parametric body model, a skeleton detection method, or a 3D registration with an annotated mean 3D body model. This will be explained hereafter and in particular with respect to the example shown in FIG. 2.

According to an embodiment of the present invention, the processing unit is configured to apply a safety margin around the identified spatial location of the lung to cover a part of the body, which is potentially affected by the respiratory motion of the patient.

Areas that bear a risk to be affected by respiratory motion are typically in and around lung. In some cases, a safety margin may cover other parts of the body, such as abdomen, which might also be affected by the respiratory motion According to a second aspect of the present invention, there is provided a magnetic resonance imaging (MRI) system, comprising:

an MRI scanner with a bore and a table for supporting a patient;

an optical camera configured to capture an optical image of the patient lying on the table before start of a diagnostic scan with the MRI scanner;

a device according to the first aspect and any associated example for detecting critical stations in a multi-station scan; and a patient-instruction device configured to provide a breathing instruction for the detected critical stations.

In some examples, the patient-instruction device may be a speaker used to prompt the patient with an automated voice to breath in, breath out, and hold the breath.

In some examples, the patient-instruction device may be an in-bore display providing visual instructions to prompt the patient to breath in, breath out, and hold the breath.

According to an embodiment of the present invention, the optical camera comprises an in-bore optical camera.

According to an embodiment of the present invention, the MRI system further comprises a controller configured to adapt a set of scan parameters per station depending on an actual anatomy and/or to apply different sets of calibration parameters for different stations. According to a third aspect of the present invention, there is provided a method for detecting critical stations in a multi-station scan, comprising:

a) receiving image data taken from a patient lying on a table before start of a diagnostic scan with a magnetic resonance imaging system, wherein the image data comprises an optical image captured by an optical camera;

b) analyzing the image data of the patient to identify a spatial location of a lung of the patient;

c) aligning the spatial location of the lung of the patient with a planned multi-station scan to identify the critical stations that are potentially affected by a respiratory motion of the patient and assigning breath-hold to the identified critical stations; and d) providing the identified critical stations.

According to an embodiment of the present invention, step b) further comprises applying a safety margin around the identified spatial location of the lung to cover a part of the body, which is also affected by the respiratory motion of the patient.

According to an embodiment of the present invention, the method further comprises providing a breathing instruction for the detected critical stations.

According to an embodiment of the present invention, the method further comprises adapting a set of scan parameters per station depending on an actual anatomy, and/or applying different sets of calibration parameters for different stations.

According to another aspect of the present invention, there is provided a computer program element for controlling a device according to the first aspect and any associated example, which when being executed by a processor is configured to carry out the method according to the third aspect and any associated example.

According to a further aspect of the present invention, there is provided a computer readable medium comprising the computer program element.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
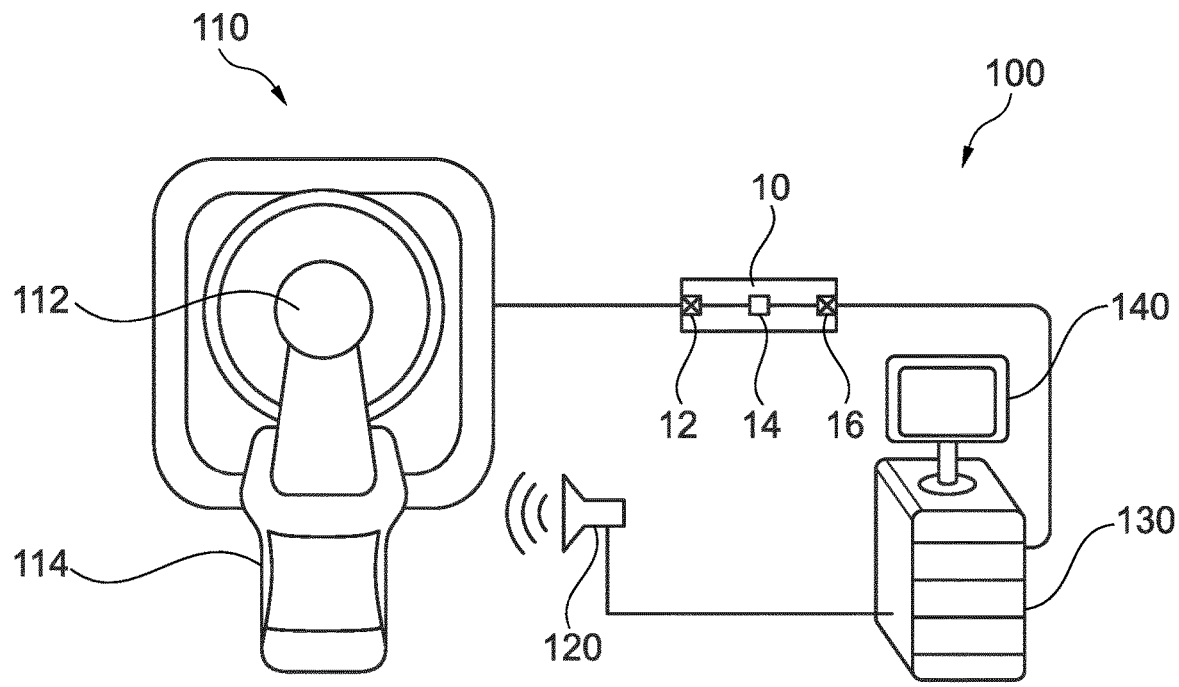
FIG. 1 shows an example of an MRI system.

FIG. 1 shows schematically and exemplary an example of a magnetic resonance imaging (MRI) system 100. The MRI system comprises an MRI scanner 110, a device 10 for detecting critical stations in a multi-station scan, and a patient-instruction device 120.

In general, the MR scanner 110 produces a polarizing magnetic field in a region commonly referred to as the magnet "bore" 112. The images to be produced by the MR scanner 110 are prescribed by selecting an appropriate nuclear magnetic resonance (NMR) imaging pulse sequence to be executed by a pulse generator. Location and orientation of the slices or three-dimensional region to be imaged are also prescribed and are determined by the particular patient anatomy that the physician wants to see during the procedure being performed.

The MRI scanner 110 measures a nuclear magnetic resonance (hereinafter referred to as "NMR") signal from protons in the patient and picks up images of a density distribution, a relaxation time distribution, etc. of protons. In the whole body imaging (whole body MRI), a table 114 on which the patient is put is repeatedly moved. MRI images of the whole body of the patient are acquired and screening examination is performed. In the multi-station imaging, the table 114 is moved stepwise to acquire a whole body image. The patient is imaged in conformity with the movement of the table while the patient is partitioned into plural stations (imaging areas). For example, in a three station CEMRA (Contrast enhanced Magnetic Resonance Angiography) study of the peripheral vasculature of a subject, these stations are generally positioned at the level of the renal artery origins, the level of the thighs, for imaging the femoral arteries, and the level of the lower legs, for imaging the popliteal arteries and their trifurcations. Complete images are acquired at each station but data acquisition is not performed when the table 114 is moved from station to station.

Overall operation of the MRI scanner 110 may be controlled by an operator from a console 130. The console 130 may be coupled to a monitor 140 on which the acquired MRI images or imager settings may be viewed or reviewed. An operator such as a medical lab technical can control via the console 130 an image acquisition run by "pointing" at specific patient anatomy and this "pointing" is sensed by the tracking coils. As a result, MRI images are acquired, combined and produced on the monitor 140, which depicts a whole body image to the physician.

The device 10 may be any computing device, including desktop and laptop computers, smartphones, tablets, etc., which is configured for detecting critical stations in a multi-station scan. In the example of FIG. 1, the components of the device 10 are shown as integrated in one single unit. However, in alternative examples, some or all components may be arranged as separate modules in a distributed architecture and connected in a suitable communication network. The device 10 and its components may be arranged as dedicated FPGAs or as hardwired standalone chips. In some examples, the device 10 or some of its components may be resident in the console 130 running as software routines.

The device 10 comprises an input unit 12, a processing unit 14, and an output unit 16. Each unit may be part of, or include an Application Specific Integrated Circuit (ASIC), an electronic circuit, a processor (shared, dedicated, or group) and/or memory (shared, dedicated, or group) that execute one or more software or firmware programs, a combinational logical circuit, and/or other suitable components that provide the described functionality.

The input unit 12 is configured to receive image data taken from a patient lying on a table before start of a diagnostic scan with the MRI scanner 110. The input unit 12 may be implemented as an Ethernet interface, a USB™ interface, a wireless interface such as a WiFi™ or Bluetooth™ or any comparable data transfer interface enabling data transfer between input peripherals and the processing unit 14. The image data taken from a patient lying on a table before start of a diagnostic scan serves as input for station planning. Examples of the image data may include a survey scan acquired with the MR scanner or an optical image from a camera.

In the example of FIG. 1, the device 10 is configured to receive a survey scan acquired with the MRI scanner 110. The image acquired from the MR survey scan is a set of three-plane, low-resolution, large field-of view localizers that are first obtained, equivalent to "scout views" in CT. The survey scan acquired with the MR system provides a low-resolution image for instance of the lung morphology based on the resonant radio-frequency signal of protons in tissues and liquids, so-called proton-MRI or 1H-MRI. The survey for a multi-station may be also a multi-station whole body scan, most of the time with two orthogonal slices. The images are stitched and then used for planning.

Figure 2:
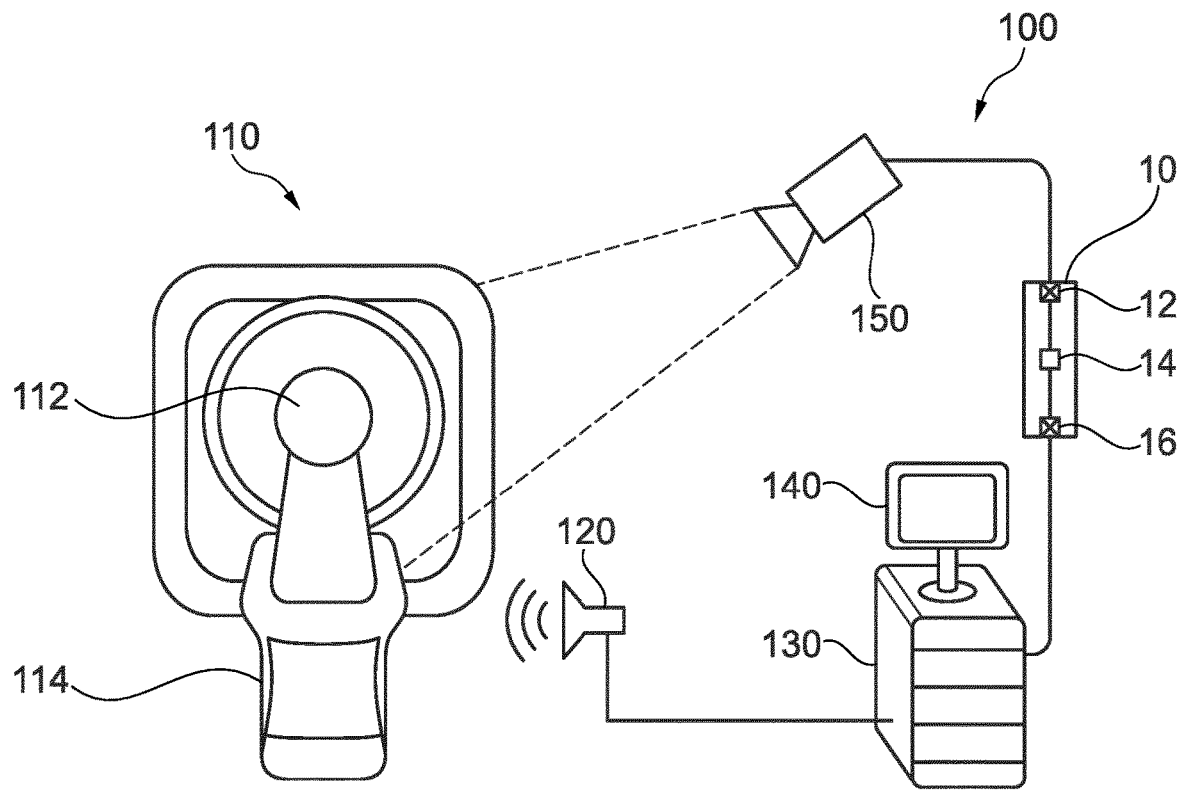
FIG. 2 shows another example of an MRI system.

In another example, as shown in FIG. 2, the device 10 may be configured to receive image data that is captured with an optical camera 150. The optical camera 150 may be a camera-based sensor, but using a three-dimensional contactless motion scanner using e.g. light detection and ranging (LIDAR), radio detection and ranging (RADAR) is also envisaged. The optical camera 150 may use visible and/or near infrared light to image the patient. The optical camera 150 may be installed somewhere above the patient to image the patient before moving the patient table into the bore. For example, the optical camera 150 may be mounted on a ceiling of the examination room, on a wall of the examination room. In this way, it is possible to analyze automatically an optical image taken from the patient directly before moving the table into the bore. For example, the optical camera 150 may be mounted on the MRI scanner. The optical camera may be calibrated to the MR system, so that any processing that is performed on the color or depth images can be transferred to the MR System with true dimensions. In an example, the optical camera 150 may be an in-bore camera, such as Philips VitalEye. The camera may be arranged inside the top left plastic casing and may focus on the subject's upper body. In this way, it is possible to analyze automatically an optical image taken from the patient positioned in the bore before start of a diagnostic scan with a magnetic resonance imaging system.

Turning back to FIG. 1, the received image data is then analyzed automatically by the processing unit 14 to identify the spatial location of the lung of the patient.

In the example of FIG. 1, this could be done, e.g., by segmenting the lung on the image acquired from an MR survey scan.

In the example of FIG. 2, different approaches are envisaged to identify the spatial location of the lung of the patient in the received optical image.

In an example, body surface approximation parametric body model, such as the SCAPE model, may be used. See for example D. Anguelov et al (2005), "SCAPE: shape completion and animation of people", ACM Trans. Graph., 24(3), 408-416. Such a model provides an accurate and scalable representation of the shape and pose of a human body. It can be used for surface matching with silhouettes derived from the sensed image data. This leads to a precise description of the patient's body, which can be used to locate the anatomical region of interest, such as the lung of the patient.

In another example, a skeleton detection method is used to detect and track patient's body. A body is described as a set of joint positions of skeleton. Coordinates of the skeleton joints are the starting point for localizing the patient's chest region and the spatial position of the lung. Elongate structures formed by patient's extremities can be followed into the image footprint the torso so as to gain clues on where the joints are situated.

In a further example, a 3D registration with an annotated, mean 3D body model may be utilized. To this end, a generalized 3D body model (e.g. CT dataset) with segmented and annotated organs can be utilized to approximate the position of the relevant anatomy of the patient, such as lungs. The generalized 3D body model is fitted and scaled to the 3D sensed body shape of the patient. The fitting and scaling can be done via 3D registration techniques. The anatomical information of the generalized and scaled 3D model can then be used to identify the anatomy of interest.

The identified spatial position of the lung using each of the above-described approaches is then aligned with the planned multi-station scan by the processing unit 14 to identify the critical stations that are potentially affected by a respiratory motion of the patient. The critical stations may comprise stations that are at least partially overlapped with the identified lung/thorax. Optionally, a safety margin may be applied around the lung/thorax to cover also parts of the body (e.g. abdomen), which are only sometimes/somewhat affected by respiratory motion.

Figures 3A, 3B, 3C, 3D:
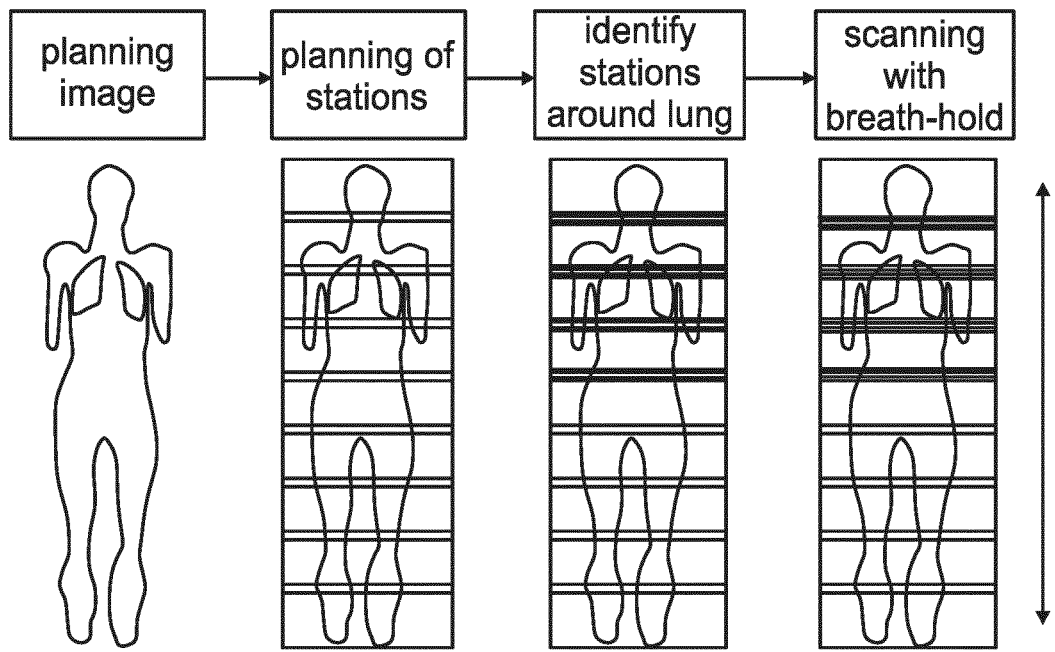
FIG. 3 shows an example of a workflow for performing the multi-station scan.

FIGS. 3A-3D schematically show an example of the workflow. FIG. 3A shows a planning image that may be acquired from an optical camera. The planning image may be displayed on the monitor 140.

FIG. 3B shows the planning of stations for multi-station MR scan. In some examples, these stations may be manually defined based on a user-supplied input. In some examples, the stations may be automatically defined based on anatomical landmarks detected on the planning image.

FIG. 3C shows the identification of the lung region and the assignment of breath-hold to the corresponding stations. These identified critical stations are indicated with a double line in FIG. 3C, but using colored lines or any other labels is also envisaged. In order to identify these critical stations, the device 10 is configured to identify the spatial position of the lung according to at least one of the above-described approaches and then align the identified spatial position of the lung with the planned multi-station scan. As shown in FIG. 3C, the identified critical stations comprise stations that cover the lung/thorax. A safety margin may be applied around the lung/thorax to cover also the abdomen of the patient, which might be affected by the respiratory motion.

FIG. 3D shows an example of the multi-station scan. The multi-station scan is performed as usual, and the combination of the images from different stations is performed as usual too. The patient-instruction device 120, such as a speaker shown in FIGS. 1 and 2, may be used to prompt the patient by an automated voice to breath in, breath out and hold the breath. In another example (not shown), the patient-instruction device 120 may be an in-bore display providing visual breathing instructions to prompt the patient to breath in, breath out and hold the breath.

Optionally, the MRI system 100 may further comprise a controller configured to adapt a set of scan parameters per station depending on an actual anatomy and/or to apply different sets of calibration parameters for different stations. In the examples shown in FIGS. 1 and 2, the controller is resident in the console 130 running as software routines. In some other examples, the controller and its components may be arranged as dedicated FPGAs or as hardwired standalone chips.

For example, the console 130 as an example of the controller may be configured to automatically adapt various scan parameters per station depending on the actual anatomy. For example, spatial resolution, field of view, number of averages, etc., may be adapted per station based on the actual anatomy. For example, a pre-trained deep learning network may be applied to derive the scan parameters from the actual anatomy and patient data (e.g. age, gender, body-mass-index, etc.). For example, deep neural networks with multiple layers between the input and output layers may be applied. The pre-trained deep learning network has been trained based on a training dataset comprising previously recorded patient data, anatomies and associated scan parameters from the same patient and/or from other patients.

The console 130 may also be configured to automatically apply different sets of calibration parameters for different stations. For example, the load of the body coil changes while moving from station to station and the applied B1 can be adjusted without repeated preparation measurements.

Figure 4:
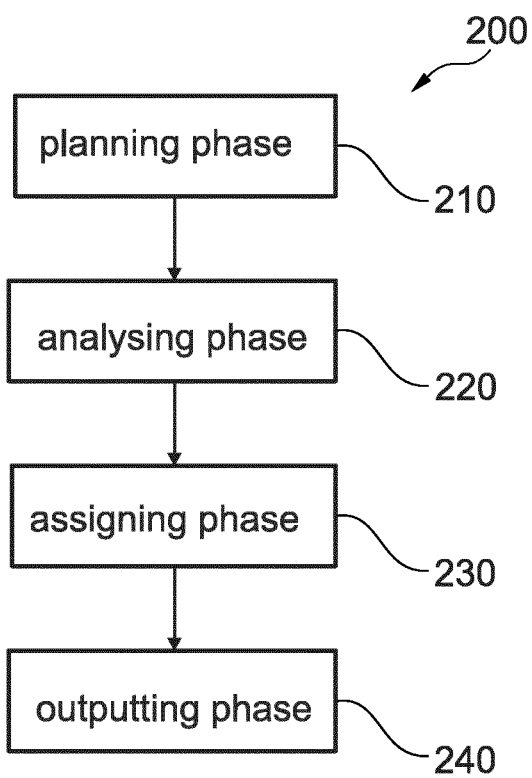
FIG. 4 shows a flow chart of a method for detecting critical stations in a multi-station scan.

With reference to FIG. 4, a flow chart is shown for a method 200 for detecting critical stations in a multi-station scan.

In step 210, i.e. step a), image data taken from a patient lying on a table before start of a diagnostic scan with a magnetic resonance imaging system is received. The image data is acquired which serves as input for station planning. This includes an optical image from a camera installed somewhere above the patient—e.g. before moving the patient table into the bore. This step may also be referred to as "planning phase".

In step 220, i.e. step b), the image data of the patient is analyzed to identify a spatial location of a lung of the patient. In other words, the planning image acquired in step a) is analyzed automatically to identify the spatial location of the lung of the patient. This could be done, e.g. by locating the thorax from the optical image, e.g. with the above-described body surface approximation parametric body model, skeleton detection method, or 3D registration with an annotated mean 3D body model. This step may also be referred to as "analyzing phase".

In step 230, i.e. step c), the spatial location of the lung of the patient is aligned with a planned multi-station scan to identify the critical stations that are potentially affected by a respiratory motion of the patient. Breath-hold is then assigned to the identified critical stations.

In this step, a multi-station scan may be manually planned by the operator or automatically planned based on the detection of anatomical landmarks. The position of the lung as identified in step b) is automatically aligned with the planned multi-station scan, i.e., all stations, which contain body parts moving due to respiration, are labelled by a corresponding software. These labelled stations are automatically set to breath-hold, such that for these stations the patient is prompted e.g. by an automated voice to breath in, breath out, and hold the breath. Optionally, a safety margin may be applied around the lung/thorax to cover also parts of the body, which are only sometimes/somewhat affected by respiratory motion. This step may also be referred to as "assigning phase".

In step 240, i.e. step d), the identified critical stations are output e.g. to the console 130 in FIGS. 1 and 2 for performing the multi-station scan. This step may also be referred to as "outputting phase".

Optionally, the method 200 may further comprise the step of instructing a patient to breath in, breath out, and/or hold the breath for the detected critical stations with the use of e.g. automated voice or visual instructions.

Optionally, the method 200 may further comprise the step of adapting a set of scan parameters (e.g. spatial resolution, field of view, number of averages) per station depending on an actual anatomy and/or applying different sets of calibration parameters for different stations.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for detecting critical stations in a multi-station scan, comprising:
an input unit;
a processing unit; and
an output unit;
wherein the input unit is configured to receive image data taken from a patient lying on a table before start of a diagnostic scan with a magnetic resonance imaging system, wherein the image data comprises an optical image captured by an optical camera;
wherein the processing unit is configured to identify a spatial location of a lung of the patient based on the received image data of the patient, to align the spatial location of the lung of the patient with a planned multi-station scan to identify critical stations that are potentially affected by a respiratory motion of the patient, and to assign breath-hold to the identified critical stations; and
wherein the output unit is configured to provide the identified critical stations.

2. The device according to claim 1,
wherein the image data comprises an optical image captured by an in-bore optical camera.

3. The device according to claim 1,
wherein the processing unit is configured to identify the spatial location of the lung of the patient by locating a thorax from the optical image based on landmark detection.

4. The device according to claim 1,
wherein the processing unit is configured to apply a safety margin around the identified spatial location of the lung to cover a part of a body of the patient, which is potentially affected by the respiratory motion of the patient.

5. A non-transitory computer readable medium storing instructions for controlling the device of claim 1 to identify the spatial location of the lung of the patient, to align the spatial location of the lung of the patient with the planned multi-station scan to identify the critical stations that are potentially affected by the respiratory motion of the patient, and to assign the breath-hold to the identified critical stations; and provide the identified critical stations at the output unit.

6. The device according to claim 1, wherein the processing unit is configured to identify the spatial location of the lung of the patient using a body surface approximation parametric body model.

7. The device according to claim 1, wherein the processing unit is configured to identify the spatial location of the lung of the patient using a skeleton detection method.

8. The device according to claim 1, wherein the processing unit is configured to identify the spatial location of the lung of the patient using 3D registration with an annotated mean 3D body model.

9. A magnetic resonance imaging (MRI) system, comprising:

an MRI scanner with a bore and a table for supporting a patient;
an optical camera configured to capture an optical image of the patient lying on the table before start of a diagnostic scan with the MRI scanner;
a processing unit for identifying critical stations in a multi-station scan that are potentially affected by a respiratory motion of the patient during the multi-station scan; and
a patient-instruction device configured to provide a breathing instruction for the patient for the identified critical stations,
wherein the processing unit is configured to:
receive image data of the optical image of the patient lying on the table via an input unit;
identify a spatial location of a lung of the patient based on the received image data of the patient;
align the spatial location of the lung of the patient with the multi-station scan to identify the critical stations, and to assign breath-hold to the identified critical stations; and
provide the identified critical stations to the patient-instruction device.

10. The MRI system according to claim 9, wherein the optical camera comprises an in-bore optical camera.

11. The MRI system according to claim 9, further comprising:
a controller configured to adapt a set of scan parameters per station of the multi-station scan depending on an actual anatomy and/or to apply different sets of calibration parameters for different stations of the multi-station scan.

12. The MRI system according to claim 9, wherein the processing unit is configured to identify the spatial location of the lung of the patient by locating a thorax from the optical image based on landmark detection.

13. A method for detecting critical stations in a multi-station scan, comprising:
receiving image data taken from a patient lying on a table before start of a diagnostic scan with a magnetic resonance imaging system, wherein the image data comprises an optical image captured by an optical camera;
identifying a spatial location of a lung of the patient based on the image data of the patient;
aligning the spatial location of the lung of the patient with a planned multi-station scan to identify the critical stations that are potentially affected by a respiratory motion of the patient and assigning breath-hold to the identified critical stations; and
providing the identified critical stations.

14. The method according to claim 13, further comprising:
applying a safety margin around the identified spatial location of the lung to cover an additional part of the patient affected by the respiratory motion of the patient.

15. The method according to claim 13, further comprising:
providing a breathing instruction for the identified critical stations.

16. The method according to claim 13, further comprising:
at least one of adapting a set of scan parameters per station depending on an actual anatomy; or
applying different sets of calibration parameters for different stations.

17. A non-transitory computer readable medium storing instructions for controlling a magnet resonance imaging (MRI) system that, when executed by a processing unit, cause the processing unit to carry out the method according to claim 13.

18. The method of claim 13, wherein identifying the spatial location of the lung of the patient based on the image data comprises applying a body surface approximation parametric body model.

19. The method of claim 13, wherein identifying the spatial location of the lung of the patient based on the image data comprises performing a skeleton detection method.

20. The method of claim 13, wherein identifying the spatial location of the lung of the patient based on the image data comprises performing 3D registration with an annotated mean 3D body model.

* * * * *